United States Patent [19]

Kawano et al.

[11] Patent Number: 5,571,717
[45] Date of Patent: Nov. 5, 1996

[54] BIOLOGICALLY PURE CULTURE OF LYOPHYLLUM ULMARIUM

[75] Inventors: Yukita Kawano; Susumu Matsui; Hideo Morita, all of Otsu, Japan

[73] Assignee: Takara Shuzo Co., Ltd., Kyoto, Japan

[21] Appl. No.: 286,255

[22] Filed: Aug. 8, 1994

[30] Foreign Application Priority Data

Aug. 16, 1993 [JP] Japan ................ 5-222323

[51] Int. Cl.$^6$ .............. C12N 1/14; C12N 1/16; C12N 1/18; A01G 1/04
[52] U.S. Cl. .............. 435/254.1; 47/1.1; 800/200
[58] Field of Search ............ 435/254.1; 47/1.1; 800/200

[56] References Cited

U.S. PATENT DOCUMENTS

| | | | |
|---|---|---|---|
| 4,940,837 | 7/1990 | Kawano et al. ........ | 800/200 |
| 5,349,120 | 9/1994 | Yoshihama et al. ........ | 47/1.1 |
| 5,349,121 | 9/1994 | Yoshihama et al. ........ | 47/1.1 |

OTHER PUBLICATIONS

Kubota et al., U.S. Application Serial No. 08/029,918, "Novel White Mushroom", filed Mar. 3, 1993.

Primary Examiner—Michael G. Wityshyn
Assistant Examiner—Blaine Lankford
Attorney, Agent, or Firm—Wenderoth, Lind & Ponack

[57] ABSTRACT

A novel multistem strain of Lyophyllum ulmarium to form fruiting bodies is disclosed. The cultivation of the novel strain of Lyophyllum ulmarium is achieved by inoculating a medium with a novel strain of Lyophyllum ulmarium and allowing the formation of fruit bodies, the novel strain of Lyophyllum ulmarium being one capable of giving 65 or more, on the average, of fruiting bodies of a stem length of 20 mm or longer when 10 g of a solid inoculum thereof is inoculated into a medium. The medium is prepared by mixing sawdust (an equivolumetric mixture of sawdust from cedar and that from beech) and rice bran at a ratio by volume of 3:1, adjusting the moisture content to 63% and pressbottling into a polypropylene wide-mouthed bottom (volume: 850 ml) in such a manner as to give 535 g of the contents, whereby fruiting bodies are formed in a conventional manner. Three strains of the multistem strain are provided.

1 Claim, No Drawings

BIOLOGICALLY PURE CULTURE OF LYOPHYLLUM ULMARIUM

DETAILED DESCRIPTION OF THE INVENTION

1. Field of Industrial Application

This invention relates to a biologically pure culture of a novel strain of *Lyophyllum ulmarium* for forming the fruiting bodies of said strain. More particularly, it relates a biologically pure culture of a multistem strain of *Lyophyllum ulmarium* for forming a large number of fruiting bodies.

2. Prior Art

Most of conventional methods for the cultivation of mushrooms are bed log cultivations with the use of, for example, Japanese oak, oak or beech logs. In these cases, the harvest frequently varies depending on weather conditions. In addition, recent lack of trees to be used as bed logs and shortage in hands for cutting trees make it difficult to obtain trees. Further, the bed log cultivation requires a long cultivation period from the inoculation of a solid inoculum to harvesting, for example, over one year and a half or two years, which inevitably results in a considerably high production cost. In recent years, artificial saw-dust cultivation, in which cultivation is effected in a bottle or a box with a culture medium obtained by blending sawdust with rice bran, for, e.g., velvet shank, oyster mushroom and nameko mushroom has been established. Thus mushrooms can be steadily harvested throughout the year. In the case of the cultivation of *Lyophyllum ulmarium*, the general trend has been toward the artificial saw-dust cultivation method in which cultivation is effected in a polypropylene wide-mouthed bottle containing a culture medium prepared by blending sawdust with rice bran, since this method is excellent in working efficiency, facilitates the management of a cultivation room, and makes it possible to steadily harvest mushrooms.

There have been publicly known several *Lyophyllum ulmarium* varieties. When cultured in a polypropylene wide-mouthed bottle (volume: 850 ml, an inner diameter of mouth: 60 mm), each of these varieties gives 40 to 50 fruiting bodies having a stem length of 20 mm or longer.

Problems to be Solved by the Invention

As discussed above, every *Lyophyllum ulmarium* variety gives 40 to 50 fruiting bodies of a stem length of 20 mm or longer when cultured in a polypropylene wide-mouthed bottle with the use of a medium prepared by blending sawdust with rice bran. However the existing *Lyophyllum ulmarium* varieties with the limited number of fruiting bodies cannot satisfy the present requirements, since the sales volume of artificially cultured *Lyophyllum ulmarium* has been increasing year by year and the application range of this mushroom has been enlarged too. Therefore, it has been required to develop a multistem strain, which is capable of forming a large number of fruiting bodies. Under these circumstances, the present invention aims at breeding a novel strain of *Lyophyllum ulmarium*, which gives an increased number of fruiting bodies when cultured in a polypropylene wide-mouthed bottle with the use of a culture medium prepared by blending sawdust with rice bran, and providing a method for the cultivation of fruit bodies with the use of this strain.

Means for Solving the Problems

The present invention can be summarized as follows. Namely, it relates to a biologically pure culture of *Lyophyllum ulmarium* having all the identifying characteristics of *Lyophyllum ulmarium*, and selected from the group consisting of *Lyophyllum ulmarium* K-8101, *Lyophyllum ulmarium* K-8103 and *Lyophyllum ulmarium* K-8104.

Throughout the present specification and claim the term "multistem strain" means that the strain produces a large number of individual or separate (not branched) stems of fruiting bodies upon cultivation. As described hereinafter the strain of the present invention is characterized by forming a much larger number of such stems than known strains of *Lyophyllum ulmarium*.

In order to breed a multistem strain of *Lyophyllum ulmarium*, the present inventors conducted cultivation tests on strains screened from those occurring in nature. 10 g of a solid inoculum of each strain was inoculated into a medium, which had been prepared by mixing sawdust (an equivolumetric mixture of sawdust from cedar and that from beech) and rice bran at a ratio by volume of 3:1, adjusting the moisture content to 63% and press-bottling into a polypropylene wide-mouthed bottle (volume: 850 ml, an inner diameter of mouth: 60 mm) in such a manner as to give 535 g of the contents, and fruiting bodies were formed in a conventional manner as described in U.S. Pat. No. 4,940,837. Then fruiting bodies having a stem length of 20 mm or longer were counted and a multistem strain was selected. Thus the present inventors have successfully fixed a novel multistem strain. Next, we performed mating with the use of the novel strain thus screened and bred as a parent strain and found novel strains of *Lyophyllum ulmarium* capable of giving 65 or more fruiting bodies of a stem length of 20 mm or longer. In particular, we have found out that a mated strain named *Lyophyllum ulmarium* K-8101, *Lyophyllum ulmarium* K-8103 and *Lyophyllum ulmarium* K-8104 by them would give 65–80 fruiting bodies (i.e., more than the existing ones by 15 to 30 fruiting bodies) of a stem length of 20 mm or longer in the cultivation method as described above, thus completing the present invention.

Now breeding of the novel strains of the present invention will be described.

1. Screening 112 fruiting bodies of *Lyophyllum ulmarium* occurring in nature were subjected to tissue separation to thereby give mycelia of 90 strains as a pure isolate. These 90 strains were then subjected to the cultivation test by the method as described above. 48 strains formed fruiting bodies in the above cultivation test. The fruiting bodies having stems of a length of 20 mm or longer were counted and *Lyophyllum ulmarium* Lu 1–13 was selected as a multistem strain. This strain has been deposited with the National Institute of Bioscience and Human-Technology, Agency of Industrial Science and Technology, Japan under the accession number of FERM P-12571.

2. Mating

Novel strains of the present invention are obtained by mating.

As described in U.S. Pat. No. 4,940,837, *Lyophyllum ulmarium* Lu 1–8 has excellent characteristics as a parent strain for creating a novel mated strain of *Lyophyllum ulmarium* being excellent in yield, growth rate and fruit body form. Thus use was made of this *Lyophyllum ulmarium* Lu 1–8 and the multistem strain *Lyophyllum ulmarium* Lu 1–13, screened and bred above, as parent strains in mating in order to give a multistem strain. *Lyophyllum ulmarium* Lu 1–8 has been deposited with the National Institute of Bioscience and Human Technology, Agency of Industrial Science and Technology, Japan under the accession number of FERM BP-1416.

Now the method for mating *Lyophyllum ulmarium* Lu 1–8 with *Lyophyllum ulmarium* Lu 1–13 will be described in greater detail. Sawdust was mixed with rice bran at a weight ratio in terms of dry matters of 9:7 and the moisture content was increased to 63% with tap water to thereby give a culture medium, which was then steam sterilized at 120° C. for 90 minutes. After cooling, this medium was inoculated with 10 g of a solid inoculum of *Lyophyllum ulmarium* Lu 1–8, which was then cultured in dark at 25° C. with the humidity of 50 to 60% for 105 days to thereby form fruiting bodies. Spores obtained from caps of the fruit bodies were allowed to germinate on a PGY agar plate medium (2% of glucose, 0.2% of peptone, 0.2% of yeast extract, 0.05% of monopotassium phosphate, 0.05% of magnesium sulfate, 2% of agar). After monospore isolation, 20 monokaryotic mycelia were obtained. In the same manner, 20 monokaryotic mycelia of *Lyophyllum ulmarium* Lu 1–13 were obtained. Subsequently, the monokaryotic mycelia of *Lyophyllum ulmarium* Lu 1–8 and those of *Lyophyllum ulmarium* Lu 1–13 were inoculated into a PGY agar plate medium facing with each other and cultured at 25° C. for 14 days to thereby effect mating. Thus 400 mated strains were obtained. Next, 10 g of a solid inoculum of each mated strain was inoculated into a medium which had been prepared by mixing sawdust (an equivolumetric mixture of sawdust from cedar and that from beech) and rice bran at a ratio by volume of 3:1, adjusting the moisture content to 63% and press-bottling into a polypropylene wide-mouthed bottle (volume: 850 ml, an inner diameter of mouth: 60 mm) in such a manner as to give 535 g of the contents. After culturing and allowing the formation of fruiting bodies in a conventional manner, fruiting bodies having stems of a length of 20 mm or longer were counted (total days of cultivation, 95 days). Thus multistem mated strains *Lyophyllum ulmarium* K-8101, *Lyophyllum ulmarium* K-8103 and *Lyophyllum ulmarium* K-8104 were obtained.

These mated strains *Lyophyllum ulmarium* K-8101, *Lyophyllum ulmarium* K-8103 and *Lyophyllum ulmarium* K-8104 have been deposited with the National Institute of Bioscience and Human Technology, Agency of Industrial Science and Technology, Japan respectively under the accession numbers of FERM P-13795, FERM P-13796 and FERM P-13797.

Now mycological properties of *Lyophyllum ulmarium* K-8101 (FERM P-13795) will be described.

(1) Malt-extract agar medium (25° C.)

With 7 days' incubation, colonies were 40 mm in diameter, showing vigorous growth. Color was white; colonies were dense, with many aerial hyphae. On the 10th day, hyphae grew in the whole petri dish. On the 17th day, dense aerial hyphae covered the entire surface of the medium. Hyphae were white.

(2) Potato-glucose agar medium (25° C.)

With 7 days' incubation, colonies were 35 mm in diameter, showing vigorous growth. Color was white; colonies were dense, with many aerial hyphae. On the 10th day, hyphae grew in the whole petri dish. On the 17th day, white hyphae covered the entire surface of the medium.

(3) Zapec-Dox agar medium (25° C.)

With 7 days' incubation, colonies were 25 mm in diameter, showing a little growth. Hyphae had many ramifications and were very thin. Little aerial hyphae. On the 17th day, hyphae grew in the whole petri dish. They were ramified, thin and white.

(4) Sabouraud agar medium (25° C.)

With 7 days' incubation, colonies were 45 mm in diameter, showing vigorous growth. Hyphae and aerial hyphae were white, cotton-like and dense but not numerous. On the 10th day, hyphae grew in the whole petri dish. Aerial hyphae were cotton-like, white and numerous.

(5) Oatmeal agar medium (25° C.)

With 7 days' incubation, colonies were 38 mm in diameter, showing vigorous growth. Hyphae were branched and stretched well while aerial hyphae little formed. On the 10th day, hyphae grew in the whole petri dish and numerous cotton-like aerial hyphae were formed. Hyphae were white.

(6) Synthetic mucor agar medium (25° C.)

With 7 days' incubation, colonies were 19 mm in diameter, showing somewhat poor growth. White hyphae grew radially. On the 17th day, hyphae grew in the whole petri dish and numerous aerial hyphae were formed. Hyphae were white.

(7) YpSs agar medium (25° C.)

With 7 days' incubation, colonies were 47 mm in diameter, showing vigorous growth. Hyphae were dense and white and many mat-like aerial hyphae were formed. On the 10th day, hyphae grew in the whole petri dish and numerous aerial hyphae were formed. Hyphae were white.

(8) Medium for phenol oxidase test (25° C.)

On the 7th day of incubation, colonies were 25 mm in diameter, showing somewhat poor growth. Hyphae were white, short and mat-like and aerial hyphae were little formed. The medium turned brown with a radius of the browning area of 39 mm. On the 17th day, colonies were 39 mm in diameter, showing a moderate growth. The browning area was 40 mm in radius.

(9) Optimum temperature for growth of mycelia

We inoculated mycelia grown on agar disk 5 mm in diameter, onto PGY agar medium plates, incubated the plates at several different temperatures, and measured the diameter of each colony after 12 days of incubation. From the results, we estimated that the optimum temperature was around 25° C. The strain could not grow at 5° C. or 35° C.

(10) Optimum pH for growth of mycelia

We inoculated mycelia grown on agar chips into PGY liquid medium (PGY agar medium from which the agar had been removed), adjusted the liquid medium to several different pH (each sample, 60 ml), and incubated the mixtures at 25° C. We measured the dry weight of the mycelia after 15 days. From the results, we estimated the optimum pH to be 7.0 to 8.0. This strain could grow at pH 3.5 to 10.0.

Now mycological properties of *Lyophyllum ulmarium* K-8103 (FERM P-13796) will be described.

(1) Malt-extract agar medium (25° C.)

With 7 days' incubation, colonies were 37 mm in diameter, showing vigorous growth. Color was white; colonies were dense, with many aerial hyphae. On the 10th day, hyphae grew in the whole petri dish. On the 17th day, dense aerial hyphae covered the entire surface of the medium. Hyphae were white.

(2) Potato-glucose agar medium (25° C.)

With 7 days' incubation, colonies were 33 mm in diameter, showing vigorous growth. Color was white; colonies were dense, with many aerial hyphae. On the 10th day, hyphae grew in the whole petri dish. On the 17th day, white hyphae covered the entire surface of the medium.

(3) Zapec-Dox agar medium (25° C.)

With 7 days' incubation, colonies were 14 mm in diameter, showing a little growth. Hyphae had many ramifications and were very thin. Little aerial hyphae. On the 17th day, hyphae grew in the whole petri dish. They were ramified, thin and white.

(4) Sabouraud agar medium (25° C.)

With 7 days' incubation, colonies were 38 mm in diameter, showing vigorous growth. Hyphae and aerial hyphae were white, cotton-like and dense but not numerous. On the 10th day, hyphae grew in the whole petri dish. Aerial hyphae were cotton-like, white and numerous.

(5) Oatmeal agar medium (25° C.)

With 7 days' incubation, colonies were 26 mm in diameter, showing vigorous growth. Hyphae were branched and stretched well while aerial hyphae little formed. On the 10th day, hyphae grew in the whole petri dish and numerous cotton-like aerial hyphae were formed. Hyphae were white.

(6) Synthetic mucor agar medium (25° C.)

With 7 days' incubation, colonies were 24 mm in diameter, showing somewhat poor growth. White hyphae grew radially. On the 17th day, hyphae grew in the whole petri dish and numerous aerial hyphae were formed. Hyphae were white.

(7) YpSs agar medium (25° C.)

With 7 days' incubation, colonies were 40 mm in diameter, showing vigorous growth. Hyphae were dense and white and many mat-like aerial hyphae were formed. On the 10th day, hyphae grew in the whole petri dish and numerous aerial hyphae were formed. Hyphae were white.

(8) Medium for phenol oxidase test (25° C.)

On the 7th day of incubation, colonies were 18 mm in diameter, showing somewhat poor growth. Hyphae were white, short and mat-like and aerial hyphae were little formed. The medium turned brown with a radius of the browning area of 35 mm. On the 17th day, colonies were 39 mm in diameter, showing a moderate growth. The browning area was 40 mm in radius.

(9) Optimum temperature for growth of mycelia

We inoculated mycelia grown on agar disk 5 mm in diameter, onto PGY agar medium plates, incubated the plates at several different temperatures, and measured the diameter of each colony after 12 days of incubation. From the results, we estimated that the optimum temperature was around 25° C. The strain could not grow at 5° C. or 35° C.

(10) Optimum pH for growth of mycelia

We inoculated mycelia grown on agar chips into PGY liquid medium, adjusted the liquid medium to several different pH (each sample, 60 ml), and incubated the mixtures at 25° C. We measured the dry weight of the mycelia after 15 days. From the results, we estimated the optimum pH to be 7.0 to 8.0. This strain could grow at pH 3.5 to 10.0.

Now mycological properties of *Lyophyllum ulmarium* K-8104 (FERM P-13797) will be described.

(1) Malt-extract agar medium (25° C.)

With 7 days' incubation, colonies were 39 mm in diameter, showing vigorous growth. Color was white; colonies were dense, with many aerial hyphae. On the 10th day, hyphae grew in the whole petri dish. On the 17th day, dense aerial hyphae covered the entire surface of the medium. Hyphae were white.

(2) Potato-glucose agar medium (25° C.)

With 7 days' incubation, colonies were 37 mm in diameter, showing vigorous growth. Color was white; colonies were dense, with many aerial hyphae. On the 10th day, hyphae grew in the whole petri dish. On the 17th day, white hyphae covered the entire surface of the medium.

(3) Zapec-Dox agar medium (25° C.)

With 7 days' incubation, colonies were 17 mm in diameter, showing a little growth. Hyphae had many ramifications and were very thin. Little aerial hyphae. On the 17th day, hyphae grew in the whole petri dish. They were ramified, thin and white.

(4) Sabouraud agar medium (25° C.)

With 7 days' incubation, colonies were 46 mm in diameter, showing vigorous growth. Hyphae and aerial hyphae were white, cotton-like and dense but not numerous. On the 10th day, hyphae grew in the whole petri dish. Aerial hyphae were cotton-like, white and numerous.

(5) Oatmeal agar medium (25° C.)

With 7 days' incubation, colonies were 36 mm in diameter, showing vigorous growth. Hyphae were branched and stretched well while aerial hyphae little formed. On the 10th day, hyphae grew in the whole petri dish and numerous cotton-like aerial hyphae were formed. Hyphae were white.

(6) Synthetic mucor agar medium (25° C.)

With 7 days' incubation, colonies were 25 mm in diameter, showing somewhat poor growth. White hyphae grew radially. On the 17th day, hyphae grew in the whole petri dish and numerous aerial hyphae were formed. Hyphae were white.

(7) YpSs agar medium (25° C.)

With 7 days' incubation, colonies were 44 mm in diameter, showing vigorous growth. Hyphae were dense and white and many mat-like aerial hyphae were formed. On the 10th day, hyphae grew in the whole petri dish and numerous aerial hyphae were formed. Hyphae were white.

(8) Medium for phenol oxidase test (25° C.)

On the 7th day of incubation, colonies were 22 mm in diameter, showing somewhat poor growth. Hyphae were white, short and mat-like and aerial hyphae were little formed. The medium turned brown with a radius of the browning area of 34 mm. On the 17th day, colonies were 39 mm in diameter, showing a moderate growth. The browning area was 40 mm in radius.

(9) Optimum temperature for growth of mycelia

We inoculated mycelia grown on agar disk 5 mm in diameter, onto PGY agar medium plates, incubated the plates at several different temperatures, and measured the diameter of each colony after 12 days of incubation. From the results, we estimated that the optimum temperature was around 25° C. The strain could not grow at 5° C. or 35° C.

(10) Optimum pH for growth of mycelia

We inoculated mycelia grown on agar chips into PGY liquid medium, adjusted the liquid medium to several different pH (each sample, 60 ml), and incubated the mixtures at 25° C. We measured the dry weight of the mycelia after 15 days. From the results, we estimated the optimum pH to be 7.0 to 8.0. This strain could grow at pH 3.5 to 10.0.

Next, to learn how to distinguish the mated strains of *Lyophyllum ulmarium* obtained in the present invention from other strains of *Lyophyllum ulmarium*, differentiation by sex factor by dual culture on an agar medium was examined on the basis of the taxonomic finding that the hyphae of different strains are different from each other. The strains of *Lyophyllum ulmarium* examined were *Lyophyllum ulmarium* IFO 9637, *Lyophyllum ulmarium* IFO 30525, *Lyophyllum ulmarium* IFO 30775, *Lyophyllum ulmarium* Lu 1–8 (FERM BP-1416), *Lyophyllum ulmarium* Lu 1–13 (FERM P-12571), *Lyophyllum ulmarium* Lu 1–2 (FERM P-12584), *Lyophyllum ulmarium* M-8171 (FERM BP-1415) and one strain of *Lyophyllum ulmarium* purchased from a supply company.

*Lyophyllum ulmarium* Lu 1–8, the above-mentioned *Lyophyllum ulmarium* Lu 1–13 and *Lyophyllum ulmarium* Lu 1–2 are strains collected respectively in Daisen (Tottori Prefecture), Urabandai (Fukushima Prefecture) and Kirizumi (Gunma Prefecture) and isolated in a pure form by the present inventors. *Lyophyllum ulmarium* M-8171 is a mated strain created via mating of *Lyophyllum ulmarium* Lu 1–8 with *Lyophyllum ulmarium* Lu 1–17. The strain purchased from a supply company is a *Lyophyllum ulmarium* strain purchased from Nippon Norin Inocula K. K. Dikaryons of each strain were excised from a stock culture (PGY agar slant medium) as a block of 3 mm×3 mm×3 mm and planted dually (interval: 2 cm) into a dikaryon block (3 mm×3 mm×3 mm) of *Lyophyllum ulmarium* K-8101, *Lyophyllum ulmarium* K-8103 or *Lyophyllum ulmarium* K-8104 at the center of a PGY agar plate medium. After culturing at 25° C. for 14 days, it was judged whether an inhibition line had been formed at the interface between the colonies or not. Table 1 shows the results (+: inhibition line was formed; –: no inhibition line was formed).

TABLE 1

| | *Lyophyllum ulmarium* | | |
|---|---|---|---|
| | K-8101 | K-8103 | K-8104 |
| *Lyophyllum ulmarium* IFO 9637 | + | + | + |
| *Lyophyllum ulmarium* IFO 30525 | + | + | + |
| *Lyophyllum ulmarium* IFO 30775 | + | + | + |
| *Lyophyllum ulmarium* Lu 1–8 | + | + | + |
| *Lyophyllum ulmarium* Lu 1–13 | + | + | + |
| *Lyophyllum ulmarium* Lu 1–2 | + | + | + |
| *Lyophyllum ulmarium* M-8171 | + | + | + |
| *Lyophyllum ulmarium* purchased from Nippon Norin Inocula K.K. | + | + | + |
| *Lyophyllum ulmarium* K-8101 | – | + | + |
| *Lyophyllum ulmarium* K-8103 | + | – | + |
| *Lyophyllum ulmarium* K-8104 | + | + | – |

As Table 1 shows, *Lyophyllum ulmarium* K-8101, *Lyophyllum ulmarium* K-8103 and *Lyophyllum ulmarium* K-8104 all formed an inhibition line with all of the test strains of *Lyophyllum ulmarium*, which clearly indicates that they are all novel strains.

As described above, every known *Lyophyllum ulmarium* variety gives 40 to 50 fruiting bodies of a stem length of 20 mm or longer when cultured in a polypropylene wide-mouthed bottle with the use of a medium prepared by blending sawdust with rice bran.

Table 2 shows the average numbers of fruiting bodies having a stem length of 20 mm or longer observed by inoculating 10 g of a solid inoculum of each novel strain of the present invention into a medium which had been prepared by mixing sawdust (an equivolumetric mixture of sawdust from cedar and that from beech) and rice bran at a ratio by volume of 3:1, adjusting the moisture content to 63% and press-bottling into a polypropylene wide-mouthed bottle (volume: 850 ml, an inner diameter of mouth: 60 mm) in such a manner as to give 535 g of the contents, and allowing the formation of fruiting bodies in a conventional manner. Table 2 also shows the data obtained by using the above-mentioned *Lyophyllum ulmarium* Lu 1–13, *Lyophyllum ulmarium* Lu 1–8, *Lyophyllum ulmarium* M-8171 and *Lyophyllum ulmarium* purchased from Nippon Norin Inocula K.K. as typical examples of known *Lyophyllum ulmarium* strains.

TABLE 2

| strain | the numbers of fruiting bodies having a stem length of 20 mm or longer* |
|---|---|
| *Lyophyllum ulmarium* K-8104 | 80 |
| *Lyophyllum ulmarium* K-8101 | 72 |
| *Lyophyllum ulmarium* K-8103 | 65 |
| *Lyophyllum ulmarium* Lu 1–13 | 58 |
| *Lyophyllum ulmarium* Lu 1–8 | 49 |
| *Lyophyllum ulmarium* M-8171 | 46 |
| *Lyophyllum ulmarium* purchased from Nippon Norin Inocula K.K. | 40 |

*: Average of 16 bottles.

As Table 2 shows, each of the novel strains of the present invention gave a larger average number of fruiting bodies of a stem length of 20 mm or longer than the conventional ones. Among all, *Lyophyllum ulmarium* K-8104, which gave 80 fruiting bodies on the average having a stem length of 20 mm or longer, namely more than the conventional strains by 30 to 40 fruiting bodies, is the most excellent multistem strain.

This strain has a particularly many stems of 20 mm or longer in length, which makes the cultivation product voluminous and highly valuable commercially.

These mated strains are comparable in yield to *Lyophyllum ulmarium* Lu 1–13, *Lyophyllum ulmarium* Lu 1–8, *Lyophyllum ulmarium* M-8171 and *Lyophyllum ulmarium* purchased from Nippon Norin Inocula K.K. The total cultivation time of each mated strain is 100 days or shorter. Compared with *Lyophyllum ulmarium* Lu 1–8 the cultivation period of which exceeds 100 days, therefore, these mated strains can be cultured within a short period of time. Fruiting bodies of these mated strain are delicious, suggesting that they have excellent properties as an edible multistem variety.

As discussed above in detail, the mated strains of the present invention can be bred by mating with the use of *Lyophyllum ulmarium* Lu 1–13. The combination of the parent strains to be used in mating can be selected from, for example, a pair of a multistem parent strain with another multistem parent strain or a pair of a multistem parent strain with another parent strain having excellent properties, depending on the purpose. Further, the novel strain of the present invention can be screened from mutants of strains which have been isolated from nature in a pure form and screened and fixed as a strain suitable for artificial cultivation. Furthermore, mating may be effected with the use of a multistem strain screened from mutants as a parent strain.

In order to culture the novel strain of *Lyophyllum ulmarium* as described above, any culture medium for artificial cultivation employed at present can be used. Also, any yield-increasing agent employed at present can be used therefor. When the novel strain of the present invention is cultured in an enriched medium or in the presence of a yield-increasing agent, the number of stems of 20 mm or longer in length increases with an increase in the yield. Furthermore, the novel strain of the present invention is applicable to any cultivation method other than the one described above aiming at giving a commercial product by taking advantage of the multistem characteristics thereof.

EXAMPLES

To further illustrate the present invention in greater detail, and not by way of limitation, the following Examples will be given.

EXAMPLE 1

A culture medium was prepared by mixing sawdust (an equivolumetric mixture of sawdust from cedar and that from beech) and rice bran at a ratio by volume of 3:1, adjusting the moisture content to 63% with tap water, stirring the mixture well and press-bottling it into a polypropylene wide-mouthed bottle (volume: 850 ml, an inner diameter of mouth: 60 mm) with an automatic bottler (Model EI8615D, mfd. Kyoei Tekkosho K.K.) in such a manner as to give 535 g of the contents. The total weight of the bottle and the contents was 580 g. After forming a hole of 1 cm in diameter from the center of the mouth of the bottle toward the bottom, the bottle was sealed with a cap and steam-sterilized at 120° C. for 90 minutes. After cooling, this medium was inoculated with 10 g of a solid inoculum of *Lyophyllum ulmarium* K-8104 (FERM P-13797), which was then cultured in dark at 25° C. with a humidity of 50 to 60% for 30 days to thereby give cultured mycelia. The mycelia were allowed to mature by further culturing under the same conditions for 40 days. After removing the cap, the mycelial layer was scratched from the surface of the medium to the depth of 1 cm and 20 ml of tap water was added thereto. After allowing the medium to absorb the water for 4 hours, the excessive water was discharged by decantation and culture was continued with light of 50 lux at 15° C. with humidity of 95% for 10 days to thereby allow primordia to form. Then the light was increased to 900 lux and culture was continued for 13 days to thereby give matured fruiting bodies. The number of stems of the matured fruiting bodies having a stem length of 20 mm or longer was 80 (on the average of 16 bottles). Thus fruiting bodies of *Lyophyllum ulmarium* of multistem strain having a good shape, regular growth and excellent qualities were obtained.

EXAMPLE 2

A culture medium was prepared by mixing sawdust (an equivolumetric mixture of sawdust from cedar and that from beech) and rice bran at a ratio by volume of 3:1, adjusting the moisture content to 63% with tap water, stirring the mixture well and press-bottling it into a polypropylene wide-mouthed bottle (volume: 850 ml, an inner diameter of mouth: 60 mm) with an automatic bottler (Model EI8615D, mfd. Kyoei Tekkosho K.K.) in such a manner as to give 535 g of the contents. The total weight of the bottle and the contents was 580 g. After forming a hole of 1 cm in diameter from the center of the mouth of the bottle toward the bottom, the bottle was sealed with a cap and steam-sterilized at 120° C. for 90 minutes. After cooling, this medium was inoculated with 10 g of a solid inoculum of *Lyophyllum ulmarium* K-8101 (FERM P-13795), which was then cultured in dark at 25° C. with a humidity of 50 to 60% for 30 days to thereby give cultured mycelia. The mycelia were allowed to mature by further culturing under the same conditions for 40 days. After removing the cap, the mycelial layer was scratched from the surface of the medium to the depth of 1 cm and 20 ml of tap water was added thereto. After allowing the medium to absorb the water for 4 hours, the excessive water was discharged by decantation and culture was continued with light of 50 lux at 15° C. with humidity of 95% for 10 days to thereby allow primordia to form. Then the light was increased to 900 lux and culture was continued for 14 days to thereby give matured fruiting bodies. The number of the matured fruiting bodies having a stem length of 20 mm or longer was 72 (on the average of 16 bottles). Thus fruiting bodies of *Lyophyllum ulmarium* of multistem strain having a good shape, regular growth and excellent qualities were obtained.

EXAMPLE 3

A culture medium was prepared by mixing sawdust (an equivolumetric mixture of sawdust from cedar and that from beech) and rice bran at a ratio by volume of 3:1, adjusting the moisture content to 63% with tap water, stirring the mixture well and press-bottling it into a polypropylene wide-mouthed bottle (volume: 850 ml, an inner diameter of mouth: 60 mm) with an automatic bottler (Model EI8615D, mfd. Kyoei Tekkosho K.K.) in such a manner as to give 535 g of the contents. The total weight of the bottle and the contents was 580 g. After forming a hole of 1 cm in diameter from the center of the mouth of the bottle toward the bottom, the bottle was sealed with a cap and steam-sterilized at 120° C. for 90 minutes. After cooling, this medium was inoculated with 10 g of a solid inoculum of *Lyophyllum ulmarium* K-8103 (FERM P-13796), which was then cultured in dark at 25° C. with a humidity of 50 to 60% for 30 days to thereby give cultured mycelia. The mycelia were allowed to mature by further culturing under the same conditions for 40 days. After removing the cap, the mycelial layer was scratched from the surface of the medium to the depth of 1 cm and 20 ml of tap water was added thereto. After allowing the medium to absorb the water for 4 hours, the excessive water was discharged by decantation and culture was continued with light of 50 lux at 15° C. with humidity of 95% for 10 days to thereby allow primordia to form. Then the light was increased to 900 lux and culture was continued for 13 days to thereby give matured fruiting bodies. The number of stems of the matured fruiting bodies having a stem length of 20 mm or longer was 65 (on the average of 16 bottles). Thus fruiting bodies of *Lyophyllum ulmarium* of multistem strain having a good shape, regular growth and excellent qualities were obtained.

REFERENCE 1

A culture medium was prepared by mixing sawdust (an equivolumetric mixture of sawdust from cedar and that from beech) and rice bran at a ratio by volume of 3:1, adjusting the moisture content to 63% with tap water, stirring the mixture well and press-bottling it into a polypropylene wide-mouthed bottle (volume: 850 ml, an inner diameter of mouth: 60 mm) with an automatic bottler (Model EI8615D, mfd. Kyoei Tekkosho K.K.) in such a manner as to give 535 g of the contents. The total weight of the bottle and the contents was 580 g. After forming a hole of 1 cm in diameter from the center of the mouth of the bottle toward the bottom, the bottle was sealed with a cap and steam-sterilized at 120° C. for 90 minutes. After cooling, this medium was inoculated with 10 g of a solid inoculum of *Lyophyllum ulmarium* Lu 1–13, which was then cultured in dark at 25° C. with a humidity of 50 to 60% for 30 days to thereby give cultured mycelia. The mycelia were allowed to mature by further culturing under the same conditions for 40 days. After removing the cap, the mycelial layer was scratched from the surface of the medium to the depth of 1 cm and 20 ml of tap water was added thereto. After allowing the medium to absorb the water for 4 hours, the excessive water was discharged by decantation and culture was continued with light of 50 lux at 15° C. with humidity of 95% for 10 days to thereby allow primordia to form. Then the light was increased to 900 lux and culture was continued for 16 days to thereby give matured fruiting bodies. The number of the matured fruiting bodies having a stem length of 20 mm or longer was 58 (on the average of 16 bottles).

Effects of the Invention

As described above, the present invention makes it possible to give a large number of fruiting bodies of *Lyophyllum ulmarium* of multistem strain which are highly applicable as a food.

We claim:
1. A biologically pure culture of *Lyophyllum ulmarium* selected from the group consisting of *Lyophyllum ulmarium* K-8101, *Lyophyllum ulmarium* K-8103 and *Lyophyllum ulmarium* K-8104.

* * * * *